United States Patent
Freudenberger (10) Patent No.: US 10,238,352 B2
(45) Date of Patent: Mar. 26, 2019

(54) RECORDING X-RAY IMAGES WITHOUT SCATTERED RADIATION

(71) Applicant: Jörg Freudenberger, Kalchreuth (DE)

(72) Inventor: Jörg Freudenberger, Kalchreuth (DE)

(73) Assignee: Siemens Healthcare GmbH, Erlangen (DE)

(*) Notice: Subject to any disclaimer, the term of this patent is extended or adjusted under 35 U.S.C. 154(b) by 282 days.

(21) Appl. No.: 15/168,274

(22) Filed: May 31, 2016

(65) Prior Publication Data

US 2016/0354046 A1    Dec. 8, 2016

(30) Foreign Application Priority Data

Jun. 2, 2015 (DE) .................. 10 2015 210 174

(51) Int. Cl.
 G21K 1/00 (2006.01)
 A61B 6/00 (2006.01)

(52) U.S. Cl.
 CPC .......... *A61B 6/4291* (2013.01); *A61B 6/5252* (2013.01)

(58) Field of Classification Search
 CPC ........ G21K 1/025; G21K 1/10; A61B 6/4291; A61B 6/5252; A61B 6/5258
 See application file for complete search history.

(56) References Cited

U.S. PATENT DOCUMENTS

| | | | |
|---|---|---|---|
| 6,181,773 B1 * | 1/2001 | Lee | G21K 1/025 378/154 |
| 7,070,328 B2 | 7/2006 | Geiger et al. | |
| 7,474,735 B2 | 1/2009 | Spahn | |
| 8,891,735 B2 | 11/2014 | Li et al. | |
| 2007/0053489 A1 | 3/2007 | Lu et al. | |
| 2007/0104321 A1 | 5/2007 | Spahn | |
| 2009/0214130 A1 | 8/2009 | Yamakita | |

FOREIGN PATENT DOCUMENTS

| | | |
|---|---|---|
| CN | 101296658 A | 10/2008 |
| DE | 102005052992 A1 | 5/2007 |
| DE | 102011080608 B4 | 2/2014 |
| DE | 102012217612 A1 | 4/2014 |

OTHER PUBLICATIONS

German office Action for related German Application No. 10 2015 210 174.6 dated Dec. 16, 2015 with English Translation.
Chinese Office Action for Chinese Patent Application No. 201610384518.9, dated Aug. 28, 2018.

* cited by examiner

*Primary Examiner* — Don Wong
(74) *Attorney, Agent, or Firm* — Lempia Summerfield Katz LLC (57) ABSTRACT

A method for generating x-ray images of an examination object is described. In the method, x-rays are emitted in a direction of an x-ray detector, wherein an examination object is arranged between the x-ray detector and an x-ray source emitting the x-rays. An anti-scatter grid, which is arranged between the examination object and the x-ray detector, is moved across the detection surface of the x-ray detector. X-ray detector signals are acquired with temporal and spatial resolution, the x-ray detector signals including the intensity of the x-rays incident on the x-ray detector. The x-ray detector signals are evaluated taking into account a temporal variation of the acquired intensity of the x-ray detector signals caused by the movement of the anti-scatter grid. An x-ray imaging apparatus is also described.

18 Claims, 4 Drawing Sheets

RECORDING X-RAY IMAGES WITHOUT SCATTERED RADIATION

This application claims the benefit of DE 10 2015 210 174.6, filed on Jun. 2, 2015, which is hereby incorporated by reference in its entirety.

TECHNICAL FIELD

The embodiments relate to a method for generating x-ray images of an examination object. Moreover, the embodiments relate to an x-ray imaging apparatus for generating x-ray images of an examination object.

BACKGROUND

Image data, which may be used to visualize an imaged examination object, is generated with the aid of modern imaging methods. The imaging methods are often based on the acquisition of x-ray radiation. During the visualization with the aid of x-ray radiation, x-ray radiation impinges on an examination object. The x-rays are absorbed to a different extent depending on the structural build of the examination object. The transmitted component of the x-ray radiation is captured on a projection surface or detector surface of an x-ray detector. The inner structures of the examination object, in particular the skeleton of a patient, may be deduced on the basis of the different local intensities of the x-ray radiation acquired at the projection surface of the x-ray detector. Here, bones absorb particularly large amounts of radiation such that little radiation arises at the corresponding points on the detector surface and these points are also only blackened a little in a pictorial representation. Therefore, skeleton parts appear bright in a pictorial representation while regions of the body that absorb little radiation, (e.g., soft tissue), appear dark.

However, x-ray radiation is not only absorbed in the examination object during the imaging with the aid of x-ray radiation; a significant component of the x-ray radiation is also scattered in the respective examination object itself, especially in the case of a thick examination object. The image contrast is reduced and hence image quality is impaired as a result of the occurrence of these scattered rays.

In order to reduce the described influence of the scattered radiation, a conventional imaging x-ray system also includes an anti-scatter grid for reducing the scattered radiation, in addition to an x-ray emitter with an x-ray source and an x-ray detector. A conventional anti-scatter grid, which is also referred to as anti-scatter grating, includes scattered radiation lamella with a large line number. The anti-scatter grid is arranged between the examination object and the x-ray detector in such a way that the radiation scattered by the examination object is absorbed by the scattered radiation lamellas. Such a grid may include lead or another strongly absorbing material and the regions between the grid structure includes a stabilizing, less absorbing material such as paper and aluminum.

There are also anti-scatter grids with cutouts between the grid structures. These anti-scatter grids are advantageous in that less radiation is absorbed by the anti-scatter grid as a result of the cutouts, as a result of which a lower patient dose emerges in the case of the same image quality. These grid structures, however, appear in the images acquired by the x-ray detectors in x-ray imaging when using such anti-scatter grids as a result of the very different absorption of the cutouts compared to the grid lamellas of the grid structures, the appearing grid structures, however, adversely affecting the image reproduction there. Conventionally, complex correction algorithms are used to eliminate these interfering images of the grid structures.

Another option for avoiding the imaging of the grid structures includes using a moving anti-scatter grid with a low line number. Moving the anti-scatter grid avoids spatially dependent differences of the x-ray intensity corresponding to the grid structures being imaged on the x-ray detector.

Alternatively, anti-scatter grids are also omitted and the resulting scattered radiation component in the imaging is subsequently removed by calculation on the basis of model considerations. Furthermore, it is also possible prior to imaging to calibrate the brightness variations or brightness differences caused on the x-ray detector by the grid and thus compensate these during the image evaluation.

Moreover, attempts are conventionally made to reduce the interfering imaging of the grid structures with the aid of suitable grid geometries. This is possible, in particular, by using grids with a very high number of grid lamellas per millimeter.

SUMMARY AND DESCRIPTION

The scope of the present invention is defined solely by the appended claims and is not affected to any degree by the statements within this summary. The present embodiments may obviate one or more of the drawbacks or limitations in the related art.

It is an object of the present embodiments to develop a method and a device, by which it is possible to undertake x-ray imaging with a good image quality and, at the same time, a reduced radiation exposure of the patient and reduced outlay for the imaging.

This object is achieved by a method for generating x-ray images of an examination object and by an x-ray imaging apparatus.

In the method for generating x-ray images of an examination object, x-rays are emitted in the direction of an x-ray detector from an x-ray source, wherein an examination object is arranged between the x-ray detector and the x-ray source. By way of example, the examination object may be a human or an animal. The object may also be any other tangible article to be examined in more detail. An anti-scatter grid, which is arranged between the examination object and the x-ray detector, is moved across the detection surface of the x-ray detector. Expressed differently, the anti-scatter grid is moved in a transverse direction in relation to the irradiation direction of the examination object and of the x-ray detector. Here, a sensor surface of the x-ray detector facing the x-ray source and the x-ray beam generated by the x-ray source is understood to be a detection surface. If an x-ray beam from the x-ray source is incident on the detection surface, a sensor event is triggered or an energy quantum is deposited, which is acquired by downstream evaluation electronics. An anti-scatter grid may refer to a structured element that absorbs x-rays and has the property of absorbing scattered rays and hence parallelizing the direction of the x-rays transmitted through the examination object. There is an acquisition of x-ray detector signals with temporal and spatial resolution, the x-ray detector signals including the intensity of the x-rays incident on the x-ray detector in a manner dependent on location and time. Expressed differently, the x-ray detector signals include information in respect of the intensity of the x-rays that were incident on the x-ray detector. So-called attenuation values, which quantitatively reproduce the attenuation, caused by the examination object and the anti-scatter grid, of the x-rays emitted by the x-ray source, are complementary to the acquired intensity.

The x-ray detector signals are evaluated taking into account a temporal variation of the acquired intensity of the x-ray detector signals caused by the movement of the anti-scatter grid. That is to say, the component of the measured x-ray detector signals, which is caused by the moving anti-scatter grid, is taken into account and may be at least partly eliminated when establishing a corrected intensity of the acquired x-rays or corrected attenuation values.

The x-ray apparatus for generating x-ray images of an examination object includes an x-ray detector for acquiring the intensity of the x-rays incident on the x-ray detector with temporal and spatial resolution. An x-ray source for emitting x-rays in the direction of the x-ray detector and an examination object situated between the x-ray detector and the x-ray source is also part of the x-ray apparatus. The x-ray apparatus moreover includes an anti-scatter grid, which is arranged between the examination object and the x-ray detector. An actuator for moving the anti-scatter grid in the transverse direction to the detection surface of the x-ray detector is also part of the x-ray apparatus. Furthermore, the x-ray apparatus includes a control apparatus for actuating the actuator. For example, control commands are provided to the actuator by the control apparatus to move the anti-scatter grid in a predetermined manner, e.g., across the x-ray detector surface with a predetermined speed. The x-ray apparatus also has an evaluation unit for processing an x-ray detector signal taking into account a temporal variation of the acquired intensity of the x-ray detector signal caused by the movement of the anti-scatter grid.

Individual components of the x-ray apparatus may also be embodied in the form of software components. In particular, this relates to the evaluation unit. In principle, this component may also be partly realized in the form of software-assisted hardware, (e.g., as FPGAs or the like), particularly if this relates to particularly fast calculations. Likewise, required interfaces may be embodied as software interfaces, for example, if this only relates to taking over data from other software components. They may also be embodied as interfaces constructed in terms of hardware, which are actuated by suitable software.

The realization largely in terms of software is advantageous in that previously used x-ray apparatuses may also be upgraded by way of a software update in order to operate in the manner according to the embodiments described herein. In this respect, the object is also achieved by a corresponding computer program product including a computer program, which is directly loadable into a storage apparatus of a control apparatus of an x-ray apparatus of an x-ray system, including program sections for executing all acts of the method when the program is executed in the x-ray apparatus. In addition to the computer program, such a computer program product may include, when necessary, additional components (e.g., documentation components), and also hardware components (e.g., hardware keys such as dongles, etc.) for using the software.

A computer readable medium, e.g., a memory stick, a hard disk drive, or any other transportable or securely installed data medium, on which the program sections of the computer program, which are readable and executable via a computer unit, are stored, serves for the purposes of transportation to the x-ray apparatus and/or of storage on or in the x-ray device. By way of example, to this end, the computer unit may have one or more cooperating microprocessors or the like.

In one refinement of the method, the anti-scatter grid is moved orthogonally with respect to a normal of the sensor surface or detection surface of the x-ray detector and/or the propagation direction of the x-rays. That is to say, the movement of the anti-scatter grid may be orthogonal to the propagation direction of the x-ray radiation emitted by the x-ray source. Here, the anti-scatter grid itself may be aligned orthogonally with respect to the propagation direction of the x-ray radiation, e.g., in such a way that the unscattered component of the transmitted x-ray radiation is also transmitted through the anti-scatter grid.

In one refinement of the method, the anti-scatter grid is moved at a constant speed. A constant movement of the anti-scatter grid is advantageous in that, in the case of a constant spacing of the grid lamellas, the interference signals caused by the anti-scatter grid occur at fixed time intervals and they may be eliminated more easily from the overall spectrum of the acquired x-ray detector signals within the scope of an evaluation. In this refinement, the interference signals occur periodically and they may easily be identified within a spectral analysis. If a periodic signal with a known frequency is generated as an interference signal on each pixel of the detector, it is also possible to use grids with worse homogeneity, e.g., with grid spacings, roughnesses, etc., varying locally over the grid surface. By way of example, in such a refinement, it is also possible to dispense with a calibration of the x-ray system for reacting to bending of the grid in different positions of the x-ray system.

The anti-scatter grid is periodically moved to and fro across the normal of the detector surface of the x-ray detector in the method. Thus, the movement direction of the anti-scatter grid is changed at fixed time intervals. In this refinement, the extent of the displacement of the anti-scatter grid may be restricted in the transverse direction. In addition, the dimensions of the anti-scatter grid may thus be restricted to the respectively current imaging region.

In a particularly practical variant of the method, the anti-scatter grid is moved to and fro at a constant movement frequency. In combination with a constant grid spacing, a sharp maximum restricted to one frequency emerges for the spectrum of the interference signal as a result of the grid movement in this embodiment, which is easily acquirable and easy to eliminate by computation. In this context, the spectrum of the interference signal and of the x-ray signal may be understood to mean not the energy distribution of the x-ray radiation but a spectrum of the intensity of the x-ray radiation, which is dependent on the time profile of the intensity of the x-rays and hence, in particular, on temporal changes in the intensity of the x-rays.

Particularly, the movement frequency of the anti-scatter grid in the method is lower than a recording frequency with which a series of image recordings is carried out. Together, a series of image recordings form one image recording. That is to say, the intensities of the individual partial images of a series, recorded successively in time, are combined, (e.g., added). In this refinement of the method, the interference as a result of the grid movements only occur in part of the series of image recordings. This is at least the case if the grid spacing or the spacing of the individual lamellas of the anti-scatter grid includes a plurality of sensor pixels of the x-ray detector. A periodicity of the interference may be read on the basis of the series of image recordings. Individual intensity variations, which are triggered by the movement of the anti-scatter grid, are acquired with a sufficient time resolution.

In a manifestation, the individual images of a series of image recordings are recorded during the time intervals in which the grid is moved with constant speed. No image is recorded at times at which the movement direction of the grid is reversed. This is achieved by virtue of the start of the recording of an image series being synchronized with the grid reaching a constant speed and the recording being completed before the grid is decelerated. In this refinement, a particularly exact temporal periodicity is obtained when recording the grid structures, which, in the spectral representation, results in a particularly sharp maximum of the spectral component caused by the grid structures.

In a variant of the method, during the evaluation of the x-ray detector signals, a transformation of the x-ray detector signals is carried out from the time domain into the frequency space. Furthermore, the signal component whose frequency lies at the frequency of the movement of the anti-scatter grid, e.g., the spectral component of the movement of the anti-scatter grid, is filtered out. In this manner, spectral components of the detector signals caused by the grid structures are eliminated.

In a particularly advantageous refinement of the method, the filtering out of the spectral component of the movement of the anti-scatter grid is performed by calculation, wherein the calculation includes subtracting the spectral component of the movement of the anti-scatter grid from the spectrum of the x-ray detector signals.

In a variant of the method, a frequency interval, in which the frequency of the movement of the anti-scatter grid lies, is set, wherein the spectral components of the x-ray detector signals situated in the set frequency interval are filtered out. By way of example, setting of the frequency interval may be established in advance, e.g., prior to the image recording, on the basis of known measurement parameters, (e.g., a distribution of the grid spacings, a distribution of the movement speed, or a temporal variation of the frequency of the movement of the anti-scatter grid). The frequency interval may also be established after the measurement by analyzing the spectrum of the x-ray detector signals.

In a refinement of the x-ray apparatus, the anti-scatter grid has a one-dimensional grid structure with a number of grid lamellas, wherein the grid lamellas may extend orthogonally with respect to the movement direction of the anti-scatter grid. In this refinement, there are no grid structures in the image of the moved grid that appear stationary in the image and therefore may not be accessible to spectral filtering.

The anti-scatter grid of the x-ray apparatus may include cutouts between the grid lamellas in each case, where the cutouts may be filled with air and may be arranged between the grid lamellas in each case as free cutouts for the passage of the x-ray radiation. If the interstices between the grid structures are embodied as cutouts, the attenuation of the intensity of the x-ray radiation due to the anti-scatter grid is reduced, and so the exposure in terms of dose of the object to be examined, (e.g., a patient), is lower with the same image quality than may turn out in the case of solid anti-scatter grids with stronger absorption of x-rays.

Incidentally, the embodiments described herein are not restricted to plane grids and x-ray sources with parallel beams. Commercially available x-ray emitters emit from approximately a point, and so the grid lamellas may be aligned on this point in this case and the grid may be moved in a manner rotating about this point by way of suitable mechanical structures.

DETAILED DESCRIPTION

Figure 1:
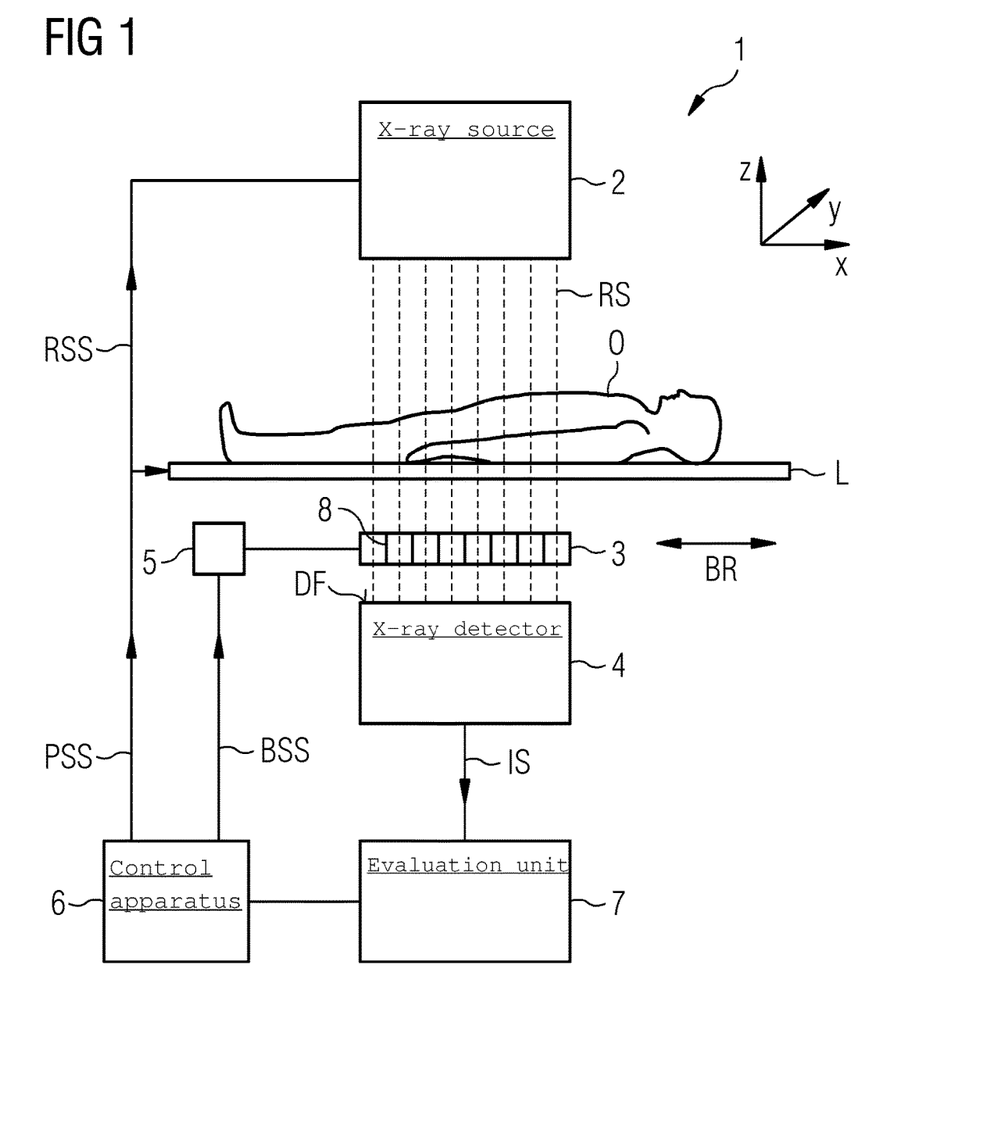
FIG. 1 depicts an x-ray system in accordance with a first exemplary embodiment.

FIG. 1 depicts an x-ray system 1 in accordance with one exemplary embodiment. The x-ray system 1 includes an x-ray source 2, by which x-rays RS are emitted in the z-direction, e.g., in the direction of an examination object O, a patient in this embodiment. The patient O is situated on a patient couch L and transilluminated by the emitted x-rays RS in the z-direction, e.g., in the direction orthogonal to the support surface of the patient couch L. Some of the x-rays RS are absorbed from the patient O. Some other x-rays RS are transmitted through the body of the patient O. Here, some of the transmitted x-rays are scattered in turn in the body of the patient O, e.g., the propagation direction of the scattered x-ray radiation deviates from the z-direction.

An x-ray detector 4, which receives the x-ray radiation transmitted through the body of the patient O and which generates an x-ray detector signal with a spatial resolution and also a temporal resolution dependent on the intensity of the incident x-ray radiation, is arranged below the patient couch L when viewed in the z-direction. For example, the x-ray detector is arranged on the side of the couch L opposite to the x-ray source 2 and the patient O. By way of example, the x-ray detector may record image series with a frequency of between 0 and 200 Hz. In this way, the dose required for imaging a single image is distributed among a plurality of images of an image series. An anti-scatter grid 3 that absorbs x-rays scattered by the body of the patient O is arranged between the patient couch L and the x-ray detector 4 such that the x-rays emerging from the anti-scatter grid 3 in the direction of the x-ray detector 4 are aligned in the z-direction, e.g., orthogonal to detector surface DF of the x-ray detector 4. As depicted in FIG. 1 and, in detail, in FIG. 3, the anti-scatter grid 3 has grid lamellas 8 that extend in the y-direction, e.g., orthogonal to the propagation direction of the x-ray radiation RS and to the longitudinal direction of the patient couch L and the patient O. The individual grid lamellas 8 of the anti-scatter grid 3 are arranged at a distance from one another with the grid distance D in the x-direction, e.g., in the longitudinal direction of the patient couch L.

FIG. 1 furthermore depicts an actuator 5, by which the anti-scatter grid 3 is moved to and fro, (e.g., in a periodic manner), across the direction of the grid lamellas 8, e.g., in the x-direction, which is also denoted by BR here. By virtue of the anti-scatter grid 3 being moved in one direction BR, (e.g., in the x-direction in this case), the structures of the anti-scatter grid 3 are prevented from appearing as lines in the x-ray recording. The actuator 5 is actuated by a control apparatus 6, which transmits control signals BSS to the actuator 5, by which, e.g., a start command, a stop command, and a signal by which the speed of the anti-scatter grid is set, are transmitted to the actuator 5. The control apparatus 6 is also additionally connected to the x-ray source 2 and the patient couch L. The control apparatus 6 transmits an x-ray control signal RSS to the x-ray source 2, by which, e.g., an intensity of the x-rays of the x-ray source 2 and/or an energy of the x-rays or energy distribution of the x-rays are set. Furthermore, the control apparatus 6 transmits a position signal PSS to a positioning mechanism of the patient couch L, by which the position of the patient O may be adjusted.

Furthermore, the control apparatus 6 synchronizes the actuator 5, the x-ray source 2 and the evaluation unit 7, e.g., in such a way that the recording of an image series and the x-ray radiation generation starts when a constant speed of the grid 3 is reached.

Although the movement of the anti-scatter grid 3 avoids that the grid lamellas appear as lines extending in the y-direction in the image recording, the structure projected by the grid lamellas onto the detector surface DF now appears as a temporally periodic interference signal during the image recording. In order to compensate this interference signal, the acquired detector signal IS is processed further by an evaluation unit 7 in such a way that the interference signal caused by the grid lamellas 8 is eliminated. By way of example, a spectral component of the detector signal, which corresponds to the frequency $f_G$ of the movement of the anti-scatter grid 3, is filtered out of the image data. A spectrum may refer to a spectrum of the temporal intensity variations of the x-rays, just like in the whole application unless it expressly denotes something else. By way of example, filtering out may include a transformation of the time-dependent image data into the frequency space. Subsequently, the spectrum obtained from the transformation is examined in respect of the manifestation of a time-dependent maximum of the attenuation of the x-ray radiation (e.g., corresponding to a minimum of the acquired intensity of the x-ray radiation), which correlates with the frequency $f_G$ of the grid movement. A frequency interval $I_{FG}$ is set around the frequency $f_G$ of the grid movement in which the maximum is situated (see FIG. 5). Furthermore, spectral components of the image data that lie around the frequency $f_G$ of the movement of the anti-scatter grid 3 in the aforementioned frequency interval $I_{FG}$ are eliminated. In order to set the frequency interval $I_{FG}$, it is possible, for example, to set a threshold $A_{min}$ of the spectral attenuation $A(f)$, which is exceeded within the frequency interval $I_{FG}$. From a technical point of view, such filtering may be realized, for example, with the aid of a bandpass filter adjusted to the found frequency interval $I_{FG}$. Alternatively, filtering may also be carried out purely by a computational process after digitizing the image data. By way of example, the filtering may be realized by a computational process by a convolution of the time-dependent image data with a filter function. In the frequency space, such a convolution corresponds to the multiplication of the transformed filter function with the attenuation spectrum $A(f)$ of the image data. If the computational operation for the filtering is carried out in the frequency space, it is subsequently necessary to transform the filtered attenuation spectrum back into the time domain. Thus, image data from which the interference signal of the grid movement has been removed are obtained.

Figure 2:
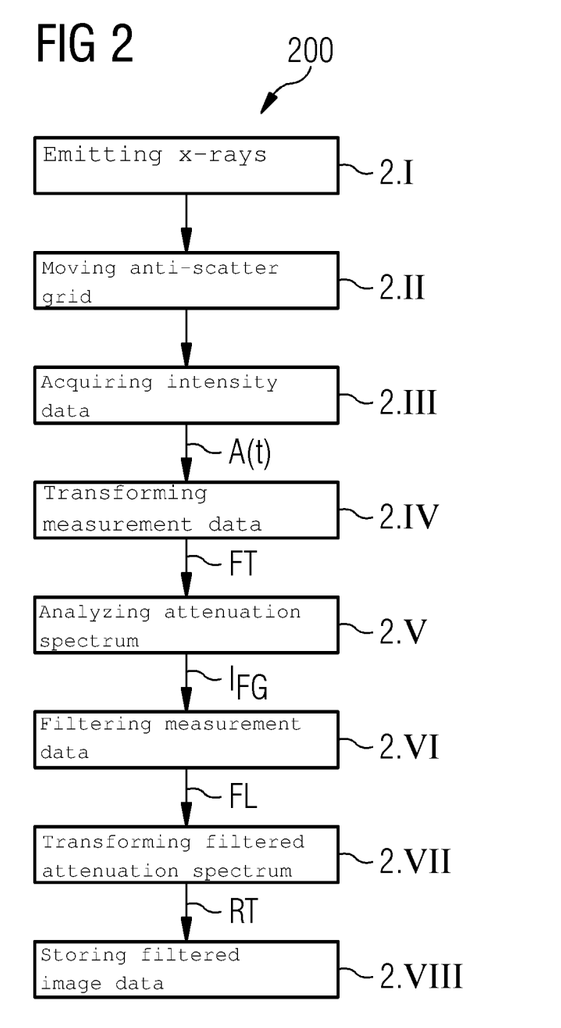
FIG. 2 depicts a flowchart, by which a method for generating x-ray images of an examination object in accordance with one exemplary embodiment is elucidated.

FIG. 2 elucidates a method 200 for generating x-ray images of an examination object O in accordance with an exemplary embodiment. In act 2.I, x-rays RS are emitted in the direction of an x-ray detector 4 and the examination object O situated between the x-ray detector 4 and an x-ray source 2. In act 2.II, an anti-scatter grid 3, which is arranged between the examination object O and the x-ray detector 2, is moved laterally in relation to the detection surface DF of the x-ray detector 4. In act 2.III, time-dependent intensity data IS of the x-ray radiation RS incident on the x-ray detector 4 is acquired for each pixel of the x-ray detector 4. Complementary to the intensity data are corresponding attenuation values $A(t)$, which include information in respect of the attenuation of the x-ray radiation by one or more objects situated between the x-ray source and x-ray detector. Subsequently, these time-dependent measurement data $A(t)$ are transformed into the frequency space at act 2.IV. In act 2.V, an analysis of the attenuation spectrum obtained by the transformation is carried out. As already mentioned, a maximum of the attenuation of the frequency $f_G$ of the grid movement in particular is analyzed, wherein, for example, the position and width thereof are established. Here, it is also possible, for example, to set a frequency interval $I_{FG}$, that corresponds to the width of the maximum and represents the frequency range to be filtered out.

In act 2.VI, filtering FL of the time-dependent measurement data $A(t)$ is undertaken in a manner dependent on the analysis carried out in act 2.V. The filtering FL may be understood to be a convolution of a function corresponding to the measured time-dependent attenuation values $A(t)$ with a filter function. In the frequency space, such a convolution simply corresponds to the product of the transformed filter function and the attenuation spectrum $a(f)$ obtained by the transformation of the function of the time-dependent attenuation values in the frequency space. In act 2.VII, there is an inverse transformation RT of the filtered attenuation spectrum into the time domain. The filtered image data obtained thus are stored in an image storage or displayed on a screen in act 2.VIII.

Figure 3:
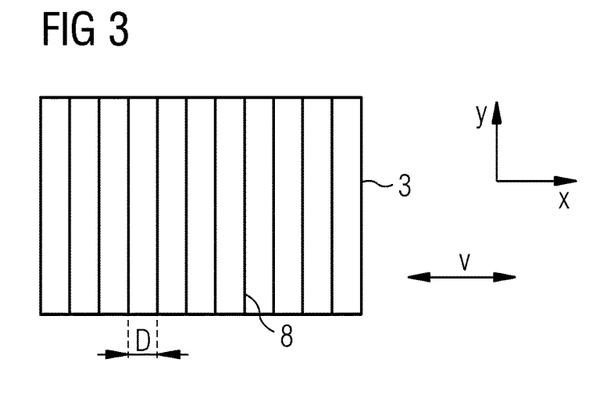
FIG. 3 depicts an illustration of an anti-scatter grid according to an exemplary embodiment.

FIG. 3 depicts an anti-scatter grid 3, as is used, for example, in the arrangement in FIG. 1, in detail. The anti-scatter grid 3 has a plurality of grid lamellas 8, which are aligned in the y-direction. The grid lamellas 8 are arranged at a distance D from one another. The distance D between the grid lamellas may be, e.g., approximately 1 mm. The thickness of the grid lamellas 8 may be between 10 and 200 μm. During an x-ray recording, the grid 3 is moved in the x-direction with the speed v. The grid 3 may be moved to and fro with a constant speed. For example, 3 mm/s may be a speed with which the grid 3 is moved. Then, the frequency $f_G=v/D$ emerges as 3 Hz. Conversely, the variation period $T_G$ of the grid 3 or the period with which the grid 3 is moved to and fro is approximately 0.33 seconds in this computational example, which may not be construed as being restrictive.

Figure 4:
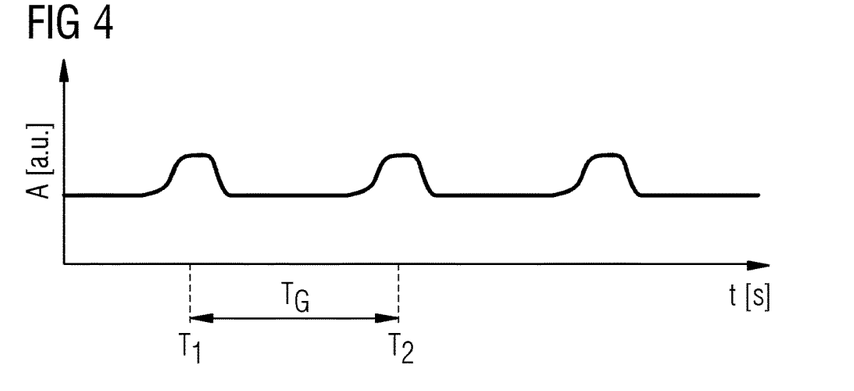
FIG. 4 depicts a graph elucidating a temporal curve of an x-ray detector signal according to an exemplary embodiment.

FIG. 4 depicts a graph that elucidates the temporal curve for measured attenuation values $A(t)$ (in arbitrary units a.u.) for a selected pixel of an x-ray detector. The attenuation values vary with time t. That is to say, they have maxima at the times T1 and T2, at which a grid lamella passes over the considered pixel of the x-ray detector. The attenuation value $A(t)$ remains substantially constant at the remaining times. The temporal distance between the two times T1, T2 corresponds to the variation period $T_G$ of the grid 3. This period $T_G$ emerges from the frequency $f_G$, with which the grid 3 is moved, as $T_G=1/f_G$.

Figure 5:
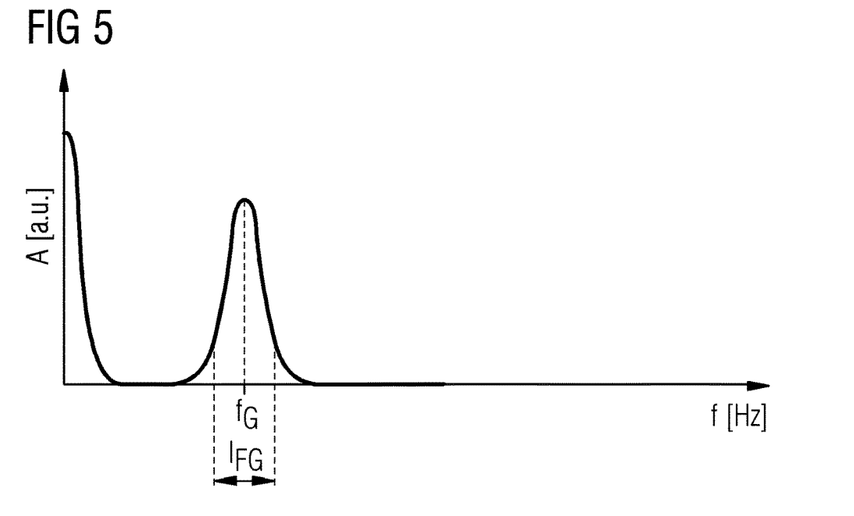
FIG. 5 depicts a graph elucidating a spectrum of attenuation values after transformation into the frequency space according to an exemplary embodiment.

FIG. 5 depicts a graph that elucidates the measured attenuation values A (in arbitrary units a.u.) as a spectrum $A(f)$ in the frequency space. A first maximum may be identified at the frequency f=0 Hz; this corresponds to the components of the spectral distribution of the attenuation values A of the x-ray image caused by the actual image recording without the movement of the anti-scatter grid 3. A second maximum may be identified at the frequency $f_G$, with which the anti-scatter grid 3 is moved to and fro. The second maximum has a certain width, which corresponds to the extent of the grid frequency interval $I_{FG}$. By way of example, the extent of this grid frequency interval $I_{FG}$ may be caused by a temporal variation of the frequency with which the grid is moved, or by a spatial variation of the grid lamella distances or the grid lamella thickness. The spectral component lying in the grid frequency interval $I_{FG}$ is removed from the attenuation spectrum A(f) in order thus to obtain an x-ray image of a patient that is not influenced by the structure of the grid lamellas. In the curve in the graph 5, the assumption is made the recording frequency is much greater than the frequency $f_G$ and therefore lies outside of the depicted frequency range.

Figure 6:
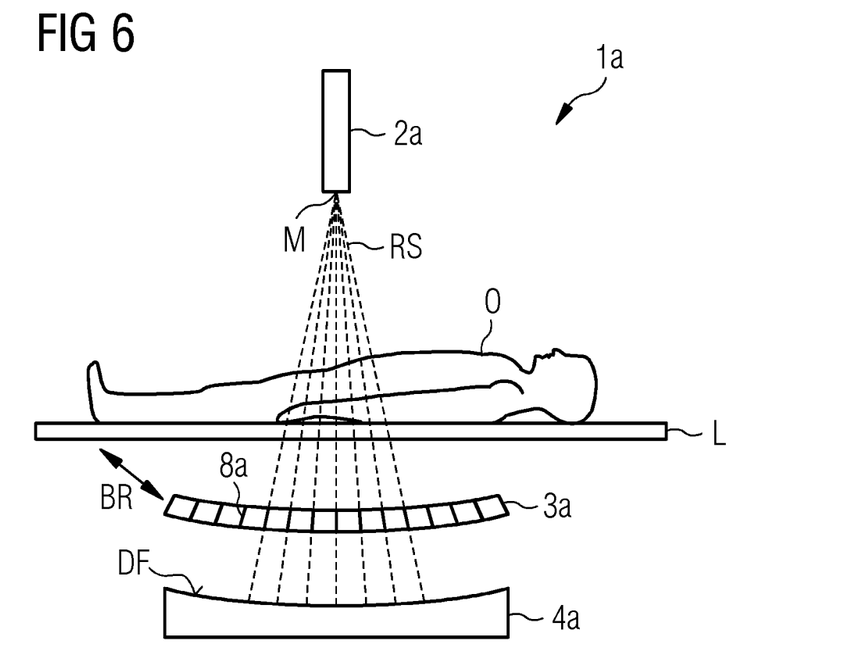
FIG. 6 depicts an x-ray system in accordance with a second exemplary embodiment.

FIG. 6 depicts details of x-ray system 1a in accordance with a second exemplary embodiment. The x-ray system 1a includes an x-ray source 2a, by which x-rays RS are emitted in the radial direction in the direction of a patient O as a fan beam from the center point M, or the axis M, which is situated at the emergence point of the x-ray radiation RS at the x-ray source 2a. The patient O is situated on a patient couch L and transilluminated by the emitted x-rays RS in the radial direction about the center point M. Some of the x-rays RS are absorbed by the patient O. Some other x-rays RS are transmitted through the body of the patient O. Here, some of the transmitted x-rays are scattered in turn in the body of the patient O, e.g., the propagation direction of the scattered x-ray radiation deviates from the radial direction.

Arranged below the patient couch L on the side of the couch L opposite to the x-ray source 2a and the patient O is an x-ray detector 4a, which receives the x-ray radiation transmitted through the body of the patient O and generates an x-ray detector signal with a spatial resolution and also a temporal resolution, which depends on the intensity of the incident x-ray radiation. The detector surface DF of the x-ray detector is slightly curved in accordance with the radial alignment of the x-ray radiation RS in this exemplary embodiment. The curvature of the detector surface DF of the x-ray detector 4a corresponds to the curvature of a circle with a radius corresponding to the distance between the center point M and the detector surface DF. Arranged between the patient couch L and the x-ray detector 4a there is an anti-scatter grid 3a, which absorbs x-rays scattered by the body of the patient O such that the x-rays RS emerging from the anti-scatter grid 3a in the direction of the x-ray detector 4a are aligned in the radial direction, e.g., orthogonally to the curved detector surface DF of the x-ray detector 4a.

In this exemplary embodiment, the anti-scatter grid 3a likewise has an arcuate curvature. The curvature of the anti-scatter grid 3a corresponds to the curvature of a circle with a radius corresponding to the distance between the center point M and the anti-scatter grid 3a. The anti-scatter grid 3a has grid lamellas 8a, which extend in the y-direction, e.g., orthogonal to the radial propagation direction of the x-ray radiation RS and to the longitudinal direction of the patient couch L and of the patient O. The individual grid lamellas 8a of the anti-scatter grid 3a are arranged at a distance from one another, e.g., with a regular grid spacing, in the arc direction of the anti-scatter grid 3a. Like the embodiment depicted in FIG. 1, the embodiment depicted in FIG. 6 likewise includes units, such as, e.g., a control apparatus, an evaluation unit, and an actuator. The anti-scatter grid 3a is moved to and fro in the arc direction BR during the image recording. In this embodiment, there is a type of rotational movement of the anti-scatter grid 3a about the center point M, e.g., the initial point of the x-ray beam, or about an axis extending perpendicular to the plane of the paper through the aforementioned center point M.

The described method and the described x-ray apparatus may find use in the field of radiography and of angiography in particular. By way of example so-called C-arm devices, or else x-ray systems with an x-ray source suspended from a support, for example a support installed in the room ceiling, may be used as x-ray apparatuses.

Reference is once again made to the fact that the above-described method 200 for generating x-ray images of an examination object and the above-described x-ray apparatus 1 are exemplary embodiments that may be varied by a person skilled in the art without departing from the scope of the invention, to the extent that the latter is predefined by the claims. Thus, the method 200 and the x-ray apparatus 1 were explained primarily on the basis of recording medical image data. However, the invention is not restricted to the application in the medical field; rather, the invention may, as a matter of principle, also be applied to the recording of images for different purposes. For the sake of completeness, reference is also made to the fact that the use of the indefinite article "a" or "an" does not preclude the relevant feature from possibly also being present a number of times. Likewise, the term "unit" does not preclude the latter from including a plurality of components that, where necessary, may also be distributed spatially.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating x-ray images of an examination object, the method comprising:
   emitting x-rays in a direction of an x-ray detector, wherein the examination object is arranged between the x-ray detector and an x-ray source emitting the x-rays;
   moving an anti-scatter grid, which is arranged between the examination object and the x-ray detector, across a detection surface of the x-ray detector;
   acquiring x-ray detector signals with temporal and spatial resolution, the x-ray detector signals comprising an intensity of the x-rays incident on the x-ray detector;
   evaluating the x-ray detector signals taking into account a temporal variation of the acquired intensity of the x-ray detector signals caused by the movement of the anti-scatter grid,
   wherein, during the evaluation of the x-ray detector signals, a transformation of the x-ray detector signals is carried out from a time domain into a frequency space, and a spectral component of the movement of the anti-scatter grid is filtered out.

2. The method of claim 1, wherein the anti-scatter grid is moved orthogonally with respect to a normal of the detection surface of the x-ray detector.

3. The method of claim 2, wherein the anti-scatter grid is moved at a constant speed.

4. The method of claim 1, wherein the anti-scatter grid is moved at a constant speed.

5. The method of claim 1, wherein the anti-scatter grid is periodically moved to and fro across a normal of the detection surface of the x-ray detector.

6. The method of claim 5, wherein the anti-scatter grid is moved to and fro at a constant movement frequency.

7. The method of claim 6, wherein the movement frequency of the anti-scatter grid is lower than a recording frequency with which a series of image recordings is carried out.

8. The method of claim 5, wherein a movement frequency of the anti-scatter grid is lower than a recording frequency with which a series of image recordings is carried out.

9. The method of claim 1, wherein the filtering out of the spectral component of the movement of the anti-scatter grid is performed by calculation, the calculation comprising subtracting the spectral component of the movement of the anti-scatter grid from a spectrum of the x-ray detector signals.

10. The method of claim 9, wherein a frequency interval, in which a frequency of the movement of the anti-scatter grid lies, is set, wherein spectral components of the x-ray detector signals situated in the set frequency interval are filtered out.

11. The method of claim 1, wherein a frequency interval, in which a frequency of the movement of the anti-scatter grid lies, is set, wherein spectral components of the x-ray detector signals situated in the set frequency interval are filtered out.

12. An x-ray imaging apparatus for generating x-ray images of an examination object, the x-ray imaging apparatus comprising:
- an x-ray detector for acquiring an intensity of x-rays incident on the x-ray detector with temporal and spatial resolution;
- an x-ray source for emitting x-rays in a direction of the x-ray detector and an examination object situated between the x-ray detector and the x-ray source;
- an anti-scatter grid arranged between the examination object and the x-ray detector;
- an actuator for moving the anti-scatter grid across a detection surface of the x-ray detector;
- a control apparatus for actuating the actuator; and
- an evaluation unit for processing x-ray detector signals taking into account a temporal variation of an acquired intensity of the x-ray detector signals caused by movement of the anti-scatter grid,
- wherein, during the processing of the x-ray detector signals, a transformation of the x-ray detector signals is configured to be carried out from a time domain into a frequency space, and a spectral component of the movement of the anti-scatter grid is configured to be filtered out.

13. The x-ray imaging apparatus of claim 12, wherein the anti-scatter grid has a one-dimensional grid structure with a number of grid lamellas.

14. The x-ray imaging apparatus of claim 13, wherein the grid lamellas extend orthogonally with respect to a movement direction of the anti-scatter grid.

15. The x-ray imaging apparatus of claim 13, wherein free cutouts for a passage of the x-ray radiation are arranged between the grid lamellas in each case.

16. The x-ray imaging apparatus of claim 14, wherein free cutouts for a passage of the x-ray radiation are arranged between the grid lamellas in each case.

17. A computer program product comprising a computer program, which is directly loadable into a storage apparatus of a control apparatus of an x-ray imaging apparatus, the computer program comprising program sections, when executed in the control apparatus of the x-ray imaging apparatus, are configured to:
- emit x-rays in a direction of an x-ray detector, wherein an examination object is arranged between the x-ray detector and an x-ray source emitting the x-rays;
- move an anti-scatter grid, which is arranged between the examination object and the x-ray detector, across a detection surface of the x-ray detector;
- acquire x-ray detector signals with temporal and spatial resolution, the x-ray detector signals comprising an intensity of the x-rays incident on the x-ray detector;
- evaluate the x-ray detector signals taking into account a temporal variation of the acquired intensity of the x-ray detector signals caused by the movement of the anti-scatter grid,
- wherein, during the evaluation of the x-ray detector signals, a transformation of the x-ray detector signals is carried out from a time domain into a frequency space, and a spectral component of the movement of the anti-scatter grid is filtered out.

18. A computer readable medium, on which program sections readable and executable via a computer unit are stored, wherein, when the program sections are executed by the computer unit, the program sections are configured to:
- emit x-rays in a direction of an x-ray detector, wherein an examination object is arranged between the x-ray detector and an x-ray source emitting the x-rays;
- move an anti-scatter grid, which is arranged between the examination object and the x-ray detector, across a detection surface of the x-ray detector;
- acquire x-ray detector signals with temporal and spatial resolution, the x-ray detector signals comprising an intensity of the x-rays incident on the x-ray detector;
- evaluate the x-ray detector signals taking into account a temporal variation of the acquired intensity of the x-ray detector signals caused by the movement of the anti-scatter grid,
- wherein, during the evaluation of the x-ray detector signals, a transformation of the x-ray detector signals is carried out from a time domain into a frequency space, and a spectral component of the movement of the anti-scatter grid is filtered out.

* * * * *